United States Patent [19]

Green et al.

[11] 4,182,742
[45] Jan. 8, 1980

[54] CHEMICAL SYNTHESIS APPARATUS HAVING DIFFERENTIAL PUMPING MEANS

[75] Inventors: Malcolm L. H. Green, Oxford; Peter Norgate, Sunbury on Thames, both of England

[73] Assignee: G. V. Planer Limited, Sunbury on Thames, England

[21] Appl. No.: 808,085

[22] Filed: Jun. 20, 1977

[30] Foreign Application Priority Data

Jun. 19, 1976 [GB] United Kingdom ............. 25538/76

[51] Int. Cl.² .......................... B01J 1/00; B01J 37/00
[52] U.S. Cl. .................. 422/199; 422/129; 422/198; 422/200; 62/55.5
[58] Field of Search ............... 23/252 R, 277 R, 279, 23/284, 285; 423/659; 260/684; 62/55.5; 422/199, 230, 238

[56] References Cited

U.S. PATENT DOCUMENTS

| 2,796,555 | 6/1957 | Connor | 353/7 |
|---|---|---|---|
| 2,946,668 | 7/1960 | Richelsen | 23/277 R |
| 3,009,828 | 11/1961 | Rogers | 423/659 |
| 3,252,652 | 5/1966 | Trendelenburg et al. | 417/48 |
| 3,494,743 | 2/1970 | Baughman et al. | 23/252 R |
| 3,957,954 | 5/1976 | Gault | 423/659 |
| 4,012,201 | 3/1977 | Powell et al. | 423/659 |
| 4,023,398 | 5/1977 | French et al. | 62/55.5 |
| 4,053,577 | 10/1977 | Arkless | 423/659 |

FOREIGN PATENT DOCUMENTS

| 1089967 | 11/1967 | United Kingdom | 23/252 R |
|---|---|---|---|
| 1093525 | 12/1967 | United Kingdom | 23/252 R |

OTHER PUBLICATIONS

Young et al, "Vapor Synthesis: . . . ", J. Appl. Chem. Biotechnol, [25], 641–651, 1975.
"Chemistry of Transition—Metal Vapors . . . ", Timms, J. Chem. Soc. (A), 1970, pp. 2526–2528.

*Primary Examiner*—Joseph Scovronek
*Assistant Examiner*—Bradley Garris
*Attorney, Agent, or Firm*—Young & Thompson

[57] ABSTRACT

Chemical synthesis apparatus includes a differential pumping device mounted in an evacuable container between an evaporant source providing a first chemical constituent and the reaction region. The differential pumping can be provided by apertured diaphragms or hollow cones, which may be cooled, mounted directly above the source which is thereby maintained at a lower pressure than the reaction region. The source may be an electron beam source or a resistively heated source arranged to direct the evaporant upwards into the reaction region and a second chemical constituent may be introduced into the reaction region. The invention also provides a method of chemical synthesis in which differential pumping is carried out between the reaction region and the source of one of the constituents.

13 Claims, 3 Drawing Figures

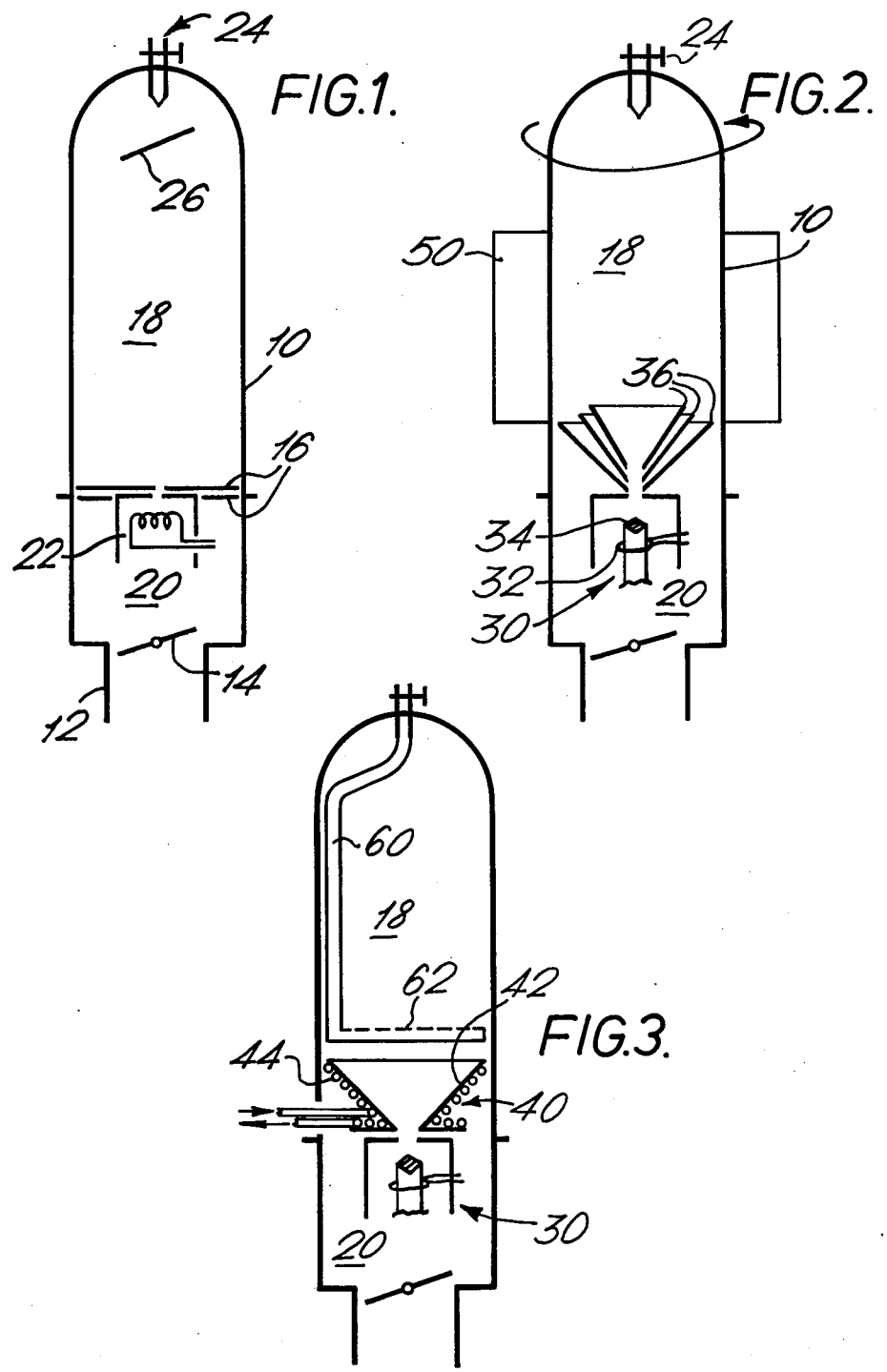

CHEMICAL SYNTHESIS APPARATUS HAVING DIFFERENTIAL PUMPING MEANS

This invention relates to chemical synthesis apparatus.

Such apparatus is used, for example where metal or other vapours produced at high temperatures e.g. in the range 200°–4000° C. are used as reactants in formation of chemical products. Typical applications are in the synthesis of organo-metallic sandwich compounds, mixed low-valence metal oxides, organic polymers which contain metal atoms, alloys, semi-conductor materials and ceramics, surface deposition of metal vapours on catalyst supports.

Examples of such synthesis occur in the co-condensation of the vapours of certain metals especially the transition metals of groups IV to VIII with organic compounds such as benzene, toluene and mesitylene. Many metal atom vapours act as catalyst precursors for the oligomerisation of organic compounds, (for example, butadiene), which is another type of application of the apparatus.

With conventional chemical synthesis apparatus the vaporisation of these metals takes place from a furnace at high temperatures whereas the desired chemical reactions often take place at low temperatures either due to chemical considerations or due to the necessity of keeping the vapour pressure of the organic material sufficiently low so that the metal vapour furnace can still operate. Thus in certain instances to ensure reasonable yield in the reaction it is necessary for the reaction to take place at a temperature at which the vapour pressure of one or more of the components is in excess of that at which the high temperature furnace, for example an electron beam evaporation source, can be suitably operated. Vapour pressure in the region of the furnace mouth should not exceed $10^{-3}$ Torr, and in the case of an electron beam source it should be less than $10^{-4}$ Torr. Depending on the nature of the material producing the vapour with an unsuitable partial pressure, the operation of the furnace could be adversely affected. In the case, for example, of an electron beam source, reaction of said vapour with the electron emitter or filament could lead to premature degradation of said filament, and in the case of any furnace, pyrolysis of said vapour on the heated filaments could lead to breakdown of the vapour and contamination of the system, loss of electrical insulation etc.

It is an object of the present invention to overcome, or at least alleviate, this problem.

According to one aspect of the present invention there is provided chemical synthesis apparatus comprising an evacuable chamber enclosing a reaction region, means mounting evaporation means for evaporating a first chemical constituent into said reaction region, differential pumping means mounted between said evaporation means and said reaction region, and inlet means for introducing a second chemical constituent into said reaction region.

According to a further aspect of the present invention, there is provided a method of chemical synthesis in which a first chemical constituent is produced from an evaporation source and introduced into a reaction region, a second chemical constituent is introduced into the reaction region, and differential pumping is effected between the evaporation source and the reaction region.

The differential pumping means ensures that the pressure around the evaporation means is maintained substantially lower than the average pressure within the enclosure at the chemical reaction region.

The apparatus has particular advantages when the evaporation means comprises an electron beam source, but it can also be used to advantage to allow the use, or to prolong the life, of other sources of the first chemical constituent, for example a resistively heated source, or to reduce pyrolytic contamination.

The invention will be further understood by reference to the drawing, which shows diagrammatically side elevations of three exemplary embodiments.

In FIG. 1, an evacuable container 10 is connected by a conduit 12 to conventional vacuum pumping equipment. A baffle valve 14 is mounted at the top of the conduit 12 to control the pressure within the container 10.

One or more diaphragms or baffles 16, comprising differential pumping means, extend across the container 10 and serve to divide it into a section 18 that comprises the reaction region and a section 20 that includes evaporation means. Apertures in the diaphragms 16 open around evaporation means 22 so as to present a larger pumping aperture to the section 20 than to the section 18, whereby the evaporation means can be maintained at a lower pressure, at say $\lesssim 10^{-4}$ Torr, than the reaction region 18, at say $5 \times 10^{-3}$ Torr.

As shown in FIG. 1, the evaporation means 22 comprises a heated resistance element, but other sources of the first constituent may be used, for example a resistively heated crucible or the electron beam source to be described with reference to FIGS. 2 and 3.

The vapour emitted by the source 22 enters the reaction region 18, where it reacts with the second chemical constituent introduced through a valve 24 at the top of the cylindrical container 10 on to a deflector vane 26.

FIG. 2 shows an apparatus employing an electron beam source 30 mounted within the container 10, whereby electrons from the emitter 32 are focused on an evaporant charge 34 to produce the first chemical constituent. In this embodiment, the differential pumping is achieved by a plurality of hollow co-axial cones 36 of different angles. It is to be understood, however, that a single cone or two or more co-axial cones of the same angle may be employed. The cones 36 are mounted with their truncated apices directly over the outlet of the evaporation source 30 so that the transit of high temperature vapour from the charge 34 through the spaces between the cones 36 results in pumping the vapour of the second chemical constituent, entering the region 18 through the valve 24, away from the furnace region in a manner analogous to the operation of a vapour diffusion pump.

FIG. 3 shows a still further differential pumping means, which comprises a cryogenic pumping device 40. As shown the device 40 takes the form of a hollow metal cone 42, opening as for the cones 36, directly on to the furnace 30, and cooled by the flow of liquid nitrogen through coiled pipe 44. It will be appreciated, however, that other cooled surfaces may be employed.

It will be appreciated that, alternatively, the electron beam source 30 of FIGS. 2 and 3 could be replaced by another type of evaporant source, such as the source 22 of FIG. 1.

The enclosure provided by the container 10 around the reaction region 18 may be immersed partially or completely in a cooling bath 50 (FIG. 2) of e.g. water, solid $CO_2$ in acetone, or liquid nitrogen etc. The upper part of the wall of the container 10 may be stationary or rotatable, as shown in FIG. 2 by way of example.

It will be appreciated that the apparatus of the invention may employ more than one of the differential means hereinbefore described.

The organic material may be introduced into the reaction region 18 via a stationary or rotary source so that it impinges on the walls of the container 10, for example as a thin film, covering areas of said wall in the region in which the vapour from the material in the furnace 20 or 30 arises. Products resulting from reaction between said organic material and the vapours emitted from the furnace may collect on the walls of the said enclosure and may be extracted if necessary after removing the coolant bath. Addition of reactants and/or extraction of products may be carried out batchwise or continuously or in a cyclical manner.

According to one example of a method using the apparatus of the invention, bis-cycloocta-1,5-diene iron, an organometallic compound is synthesised in the following manner:

Iron metal placed on the hearth of the electron beam source 30 is heated by bombardment with electrons emitted from the molybdenum filament, provision having been made to prevent molybdenum contamination of the charge by obviating any direct optical path between filament and charge. Electron emission is produced by the application of a high voltage between the filament and hearth while the filament is heated by means of passage of an electric current. In this way vapour of iron atoms is produced and projected towards the reaction region 18 where there is simultaneously introduced vapour of cyclooctadiene. The walls of the container 10 are cooled by a bath 50 of solid carbon dioxide in acetone.

Pressure in the reaction region 18 is above $10^{-3}$ Torr. A liquid nitrogen cooled metal hollow cone 42 located coaxially above the hearth cryogenically pumps the excess vapour of the cycloocta-diene thus reducing the amount entering the furnace region 20. Pumping apertures located in the base of the electron beam source are of larger area than the aperture between the source and the reaction region. The effect of these differential pumping means is to maintain the pressure within the electron beam source 30 at about $10^{-4}$ Torr notwithstanding the higher pressure in the reaction region 18. The product bis-cycloocta-1,5-diene iron synthesised is extracted as a solution from the walls of the reaction container 10 after allowing said walls to warm up to room temperature.

Similar methods may be used with the apparatus for the preparation of such compounds containing tungsten or other metals in place of the iron, as well as of other organo-metallic compounds.

As an alternative to the provision of the vane 26 of FIG. 1 for ensuring that the second constituent is not directed on to the evaporation source, other means can be employed. One example of an alternative inlet arrangement is shown in FIG. 3. The valve 24 is connected to a tube 60 that guides the second constituent down to a ring 62 around the inside of the container 10 above the cone 42. The ring 62 is apertured in its upper surface to allow the second constituent to enter the reaction region 18 in an upward direction.

We claim:

1. Chemical synthesis apparatus comprising: an evacuable chamber enclosing a reaction region and an evaporation region; evaporation means mounted in said evaporation region for producing a first chemical constituent; differential pumping means mounted in said chamber to separate said evaporation region from said reaction region, said differential pumping means, when said chamber is evacuated, maintaining residual gas pressure within said evaporation region at an appreciably lower pressure than within said reaction region and passing said evaporated first chemical constituent from said evaporation region into said reaction region, said differential pumping means comprising at least one hollow frustoconical member, means mounting said member with the smaller end thereof directly adjacent said evaporation means such that said first chemical constituent passes through said member before entering said reaction region; and inlet means mounted on said chamber for introducing a second chemical constituent into said reaction region.

2. Chemical synthesis apparatus comprising: an evacuable chamber enclosing a reaction region and an evaporation region; evaporation means mounted in said evaporation region for producing a first chemical constituent; differential pumping means mounted in said chamber to separate said evaporation region from said reaction region, said differential pumping means, when said chamber is evacuated, maintaining residual gas pressure within said evaporation region at an appreciably lower pressure than within said reaction region and passing said evaporated first chemical constituent from said evaporation region into said reaction region, said differential pumping means comprising a cooled surface arranged directly above said evaporation means whereby said first chemical constituent passes over said surface before entering said reaction region, said surface being a frustoconical surface that tapers toward said evaporation means; and inlet means mounted on said chamber for introducing a second chemical constituent into said reaction region.

3. Chemical synthesis apparatus comprising: an evacuable chamber enclosing a reaction region and an evaporation region; evaporation means mounted in said evaporation region for producing a first chemical constituent; differential pumping means mounted in said chamber to separate said evaporation region from said reaction region, said differential pumping means, when said chamber is evacuated, maintaining residual gas pressure within said evaporation region at an appreciably lower pressure than within said reaction region and passing said evaporated first chemical constituent from said evaporation region into said reaction region, said differential pumping means comprising diaphragm means extending across said chamber, said diaphragm means comprising a plurality of substantially planar, apertured diaphragms extending substantially parallel to each other, said apertures of said diaphragm means opening into said evaporation region directly adjacent said evaporation means; and inlet means mounted on said chamber for introducing a second chemical constituent into said reaction region.

4. Chemical synthesis apparatus comprising an evacuable chamber enclosing a reaction region, evaporation means for evaporating a first chemical constitutent into said reaction region, means for mounting said evaporation means in said chamber, differential pumping means comprising at least one hollow frusto-conical member mounted between said evaporation means and said reaction region, means mounting said member with the smaller end thereof directly adjacent said evaporation means such that said first chemical constituent passes through said member before entering said reaction region, and inlet means for introducing a second chemical constituent into said reaction region.

5. The apparatus of claim 4, in which said evaporation means comprises an electron beam source.

6. The apparatus of claim 4, in which said evaporation means comprises a resistively heated crucible.

7. The apparatus of claim 4, in which said inlet means comprises a valve.

8. The apparatus of claim 4, in which said inlet means extends through that portion of said chamber that encloses said reaction region and communicates between said reaction region and the exterior of said chamber.

9. Chemical synthesis apparatus comprising an evacuable chamber enclosing a reaction region, evaporation means for evaporating a first chemical constituent into said reaction region, means for mounting said evaporation means in said chamber, differential pumping means comprising a frusto-conical surface opening directly away from said evaporation means whereby said first chemical constituent passes over said surface before entering said reaction region, means cooling said frusto-conical surface, and inlet means for introducing a second chemical constituent into said reaction region.

10. The apparatus of claim 9, in which said evaporation means comprises an electron beam source.

11. The apparatus of claim 9, in which said evaporation means comprises a resistively heated crucible.

12. The apparatus of claim 9, in which said inlet means comprises a valve.

13. The apparatus of claim 9, in which said inlet means extends through that portion of said chamber that encloses said reaction region and communicates between said reaction region and the exterior of said chamber.

* * * * *